United States Patent
Rudnick et al.

(10) Patent No.: US 10,149,762 B2
(45) Date of Patent: Dec. 11, 2018

(54) MULTIPLE COMPONENT BONE VOID FILLING IMPLANT

(71) Applicant: Howmedica Osteonics Corp., Mahwah, NJ (US)

(72) Inventors: James J. Rudnick, Mahwah, NJ (US); Christopher Michael Bennett, Thomaston, GA (US); Anthony Wolverton, Atlanta, GA (US); Jason Wainwright, Thomaston, GA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 15/145,447

(22) Filed: May 3, 2016

(65) Prior Publication Data
US 2016/0242910 A1  Aug. 25, 2016

Related U.S. Application Data

(63) Continuation of application No. 13/457,869, filed on Apr. 27, 2012, now Pat. No. 9,968,455.

(51) Int. Cl.
*A61F 2/28* (2006.01)
*A61F 2/30* (2006.01)

(52) U.S. Cl.
CPC .. *A61F 2/2875* (2013.01); *A61F 2002/30331* (2013.01); *A61F 2002/30378* (2013.01);
(Continued)

(58) Field of Classification Search
CPC .. A61F 2002/30329; A61F 2002/30383; A61F 2002/30398; A61F 2220/0033; A61F 2/2875
See application file for complete search history.

(56) References Cited

U.S. PATENT DOCUMENTS

| 3,488,779 A | 1/1970 | Christensen |
|---|---|---|
| 3,720,959 A | 3/1973 | Hahn |

(Continued)

FOREIGN PATENT DOCUMENTS

| JP | 2001092950 A | 4/2001 |
|---|---|---|
| RU | 2074672 C1 | 3/1997 |

(Continued)

OTHER PUBLICATIONS

European Search Report and Written Opinion for Application No. EP 13002198 dated Jul. 26, 2013.

*Primary Examiner* — Thomas J Sweet
*Assistant Examiner* — Melissa Hoban
(74) *Attorney, Agent, or Firm* — Lerner, David, Littenberg, Krumholz & Mentlik, LLP

(57) ABSTRACT

Disclosed herein are implants and methods for filling voids in a cranium of a patient. A craniofacial implant that may be used for filling such voids may include at least first and second components each having outer and inner surfaces, the outer and inner surfaces being curved in an inferior to posterior direction and a medial to lateral direction. The first component includes a flange extending outwardly from a medial side surface thereof and the second component includes a recessed portion extending inwardly from a medial side surface thereof. The first and second components are preferably engageable to one another such that the medial side surfaces of the first and second components are adjacent one another and the flange of the first component is housed within the recessed portion of the second component.

18 Claims, 11 Drawing Sheets

(52) U.S. Cl.
CPC ............... *A61F 2002/30576* (2013.01); *A61F 2002/30599* (2013.01); *A61F 2002/30611* (2013.01); *A61F 2220/0033* (2013.01)

(56) References Cited

U.S. PATENT DOCUMENTS

| | | | |
|---|---|---|---|
| 5,053,049 A | | 10/1991 | Campbell |
| 5,195,951 A | | 3/1993 | Giampapa |
| 5,380,329 A | | 1/1995 | Elia et al. |
| 5,391,181 A | | 2/1995 | Johnson et al. |
| 5,421,831 A | | 6/1995 | Giampapa |
| 5,496,371 A | | 3/1996 | Eppley et al. |
| 5,514,179 A | | 5/1996 | Brennan |
| 5,554,194 A | | 9/1996 | Sanders |
| 5,634,944 A | | 6/1997 | Magram |
| 5,658,516 A | | 8/1997 | Eppley et al. |
| 5,693,100 A | * | 12/1997 | Pisharodi ............... A61F 2/4455 623/17.16 |
| 5,741,215 A | | 4/1998 | D'Urso |
| RE37,249 E | | 6/2001 | Leibinger et al. |
| 6,277,150 B1 | | 8/2001 | Crawley et al. |
| 6,302,884 B1 | | 10/2001 | Wellisz et al. |
| 6,395,031 B1 | * | 5/2002 | Foley ..................... A61B 17/70 623/17.11 |
| 6,551,608 B2 | | 4/2003 | Yao |
| 6,582,435 B2 | | 6/2003 | Wellisz et al. |
| 7,066,962 B2 | | 6/2006 | Swords |
| 2002/0116065 A1 | * | 8/2002 | Jackson ................. A61F 2/446 623/17.16 |
| 2002/0133166 A1 | * | 9/2002 | McKay ................. A61F 2/4601 606/99 |
| 2003/0144743 A1 | | 7/2003 | Edwards et al. |
| 2005/0107795 A1 | | 5/2005 | Morris et al. |
| 2005/0154465 A1 | * | 7/2005 | Hodges ................. A61F 2/4405 623/17.16 |
| 2006/0116682 A1 | | 6/2006 | Longo |
| 2006/0217813 A1 | | 9/2006 | Posnick et al. |
| 2006/0224242 A1 | | 10/2006 | Swords et al. |
| 2006/0241763 A1 | * | 10/2006 | Paul ........................ A61F 2/28 623/17.11 |
| 2007/0067041 A1 | | 3/2007 | Kotoske |
| 2008/0009953 A1 | | 1/2008 | Ling et al. |
| 2008/0114464 A1 | * | 5/2008 | Barnett ................. A61F 2/3868 623/20.33 |
| 2009/0099661 A1 | | 4/2009 | Bhattacharya et al. |
| 2009/0275947 A1 | | 11/2009 | Graham et al. |
| 2010/0312284 A1 | | 12/2010 | Linares |
| 2010/0324688 A1 | | 12/2010 | Doty |
| 2012/0203281 A1 | | 8/2012 | Bouliane et al. |
| 2012/0265312 A1 | | 10/2012 | Burke et al. |
| 2012/0330427 A1 | | 12/2012 | Yaremchuk |

FOREIGN PATENT DOCUMENTS

| | | | | |
|---|---|---|---|---|
| WO | | 2009126820 A1 | 10/2009 | |
| WO | WO | 2011005166 A1 * | 1/2011 | ........... A61F 2/3603 |
| WO | | 2012016200 A1 | 2/2012 | |

* cited by examiner

Gap
BUTT JOINT

BISCUIT JOINT

BEVEL JOINT

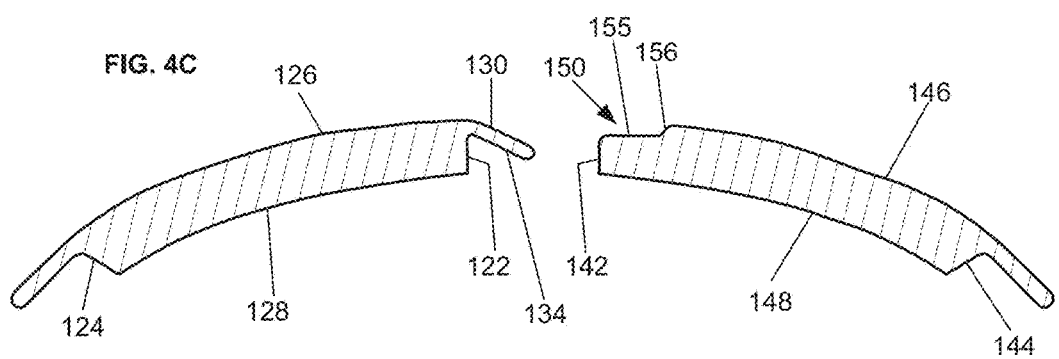
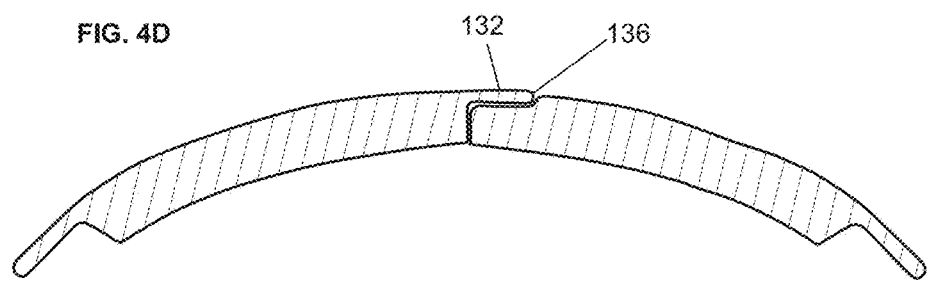

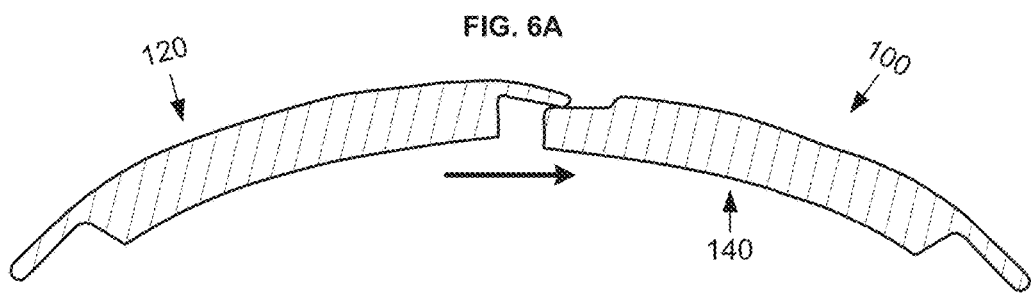
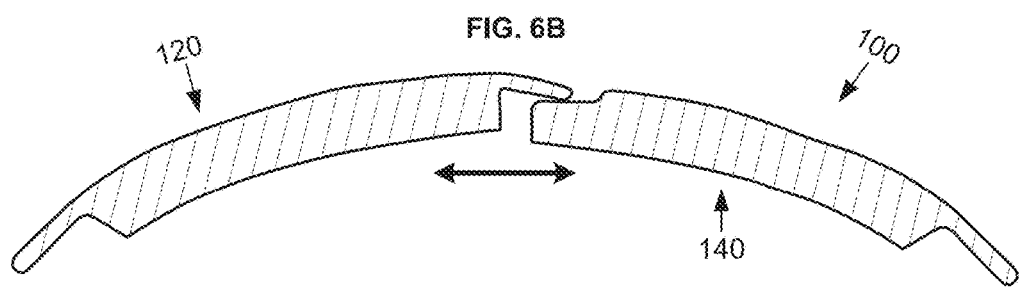
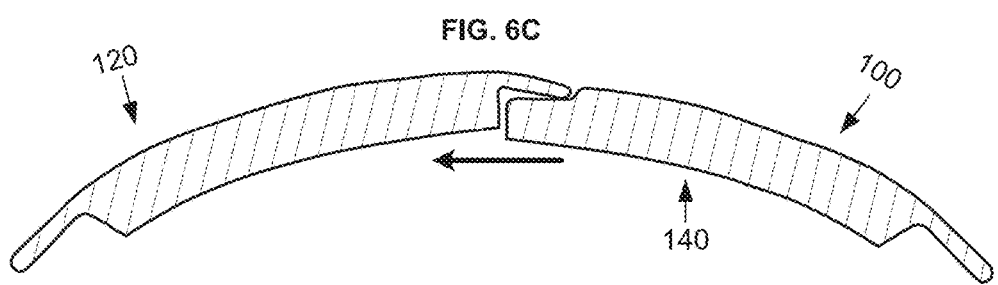

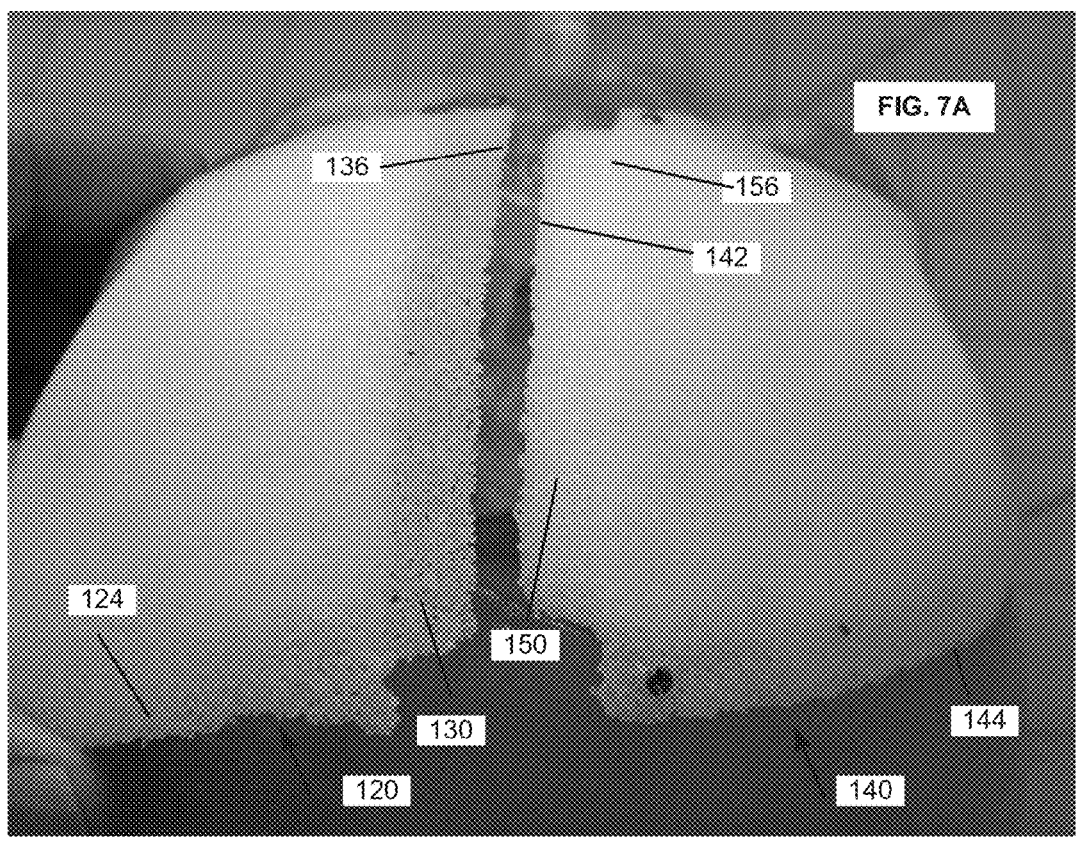

MULTIPLE COMPONENT BONE VOID FILLING IMPLANT

CROSS-REFERENCE TO RELATED APPLICATION

This application is a continuation of U.S. application Ser. No. 13/457,869, filed on Apr. 27, 2012, the disclosure of which is incorporated herein by reference.

FIELD OF THE INVENTION

The present invention relates to bone void filling implants having multiple components, and in particular it relates to the multiple components having complementary mating features for providing secure engagement between the multiple components.

BACKGROUND OF THE INVENTION

Certain congenital deformities and traumatic injuries may result in varying sized and shaped voids in bone. Severe impacts to the head could leave the frontal lobe of the cranium in need of repair, for example. Some catastrophic car accidents, for instance, may leave victims with certain bones of the cranium broken and/or crushed. If enough of the bone is crushed, a surgeon may need to remove fragments of the bone leaving what may be considered a large void in the cranium that needs to be covered and repaired. It is generally difficult to construct or form a single-component prosthesis or implant to span a large and irregularly shaped bone void.

Multiple component implants have been used to cover such bone voids in the cranium, for instance. Multiple component implants for filling voids in bone have utilized butt-type or bevel-type joint designs, for example. Each of these designs generally result in at least some gap remaining between adjacent components after fixation. Fixation members, such as plates and screws, for example, may be added to these designs to secure the engagement between adjacent components and provide rigidity to the assembled construct. Across the joint line; however, these fixation members may be noticeable under the skin and only secure the implant components at specific sites resulting in weaker areas along the joint line where the fixation members are not located.

The aforementioned butt-type and bevel-type may therefore result in uneven loading such that motion and abrasion between adjacent components can occur. Further, uneven loading in a butt-type joint can cause deflection of components in multiple component implants. With bevel-type joints, uneven loading can cause deflection of an inner unsupported component. Further still, there is generally always some degree of gap between adjacent components in either butt-type or bevel-type joints.

Other joints for affixing adjacent components together for filling voids in bone have been used. What may be referred to as a biscuit-type joint, for example, is generally a three-piece joint that requires secondary operations to fabricate. Such joints are generally not preferred over longer joint lengths. Generally, the multiple components used in such joints are difficult to intraoperatively align and assemble.

There exists a need for bone void filling implants having multiple components wherein the components have complementary mating features for providing secure engagement along substantially the entire joint line of the assembled components. Further, there exists a need for such multiple component bone void filling implants to be effectively assembled without the need for the addition of fixation plates and screws along the joint line.

BRIEF SUMMARY OF THE INVENTION

Multiple component implants are generally employed for several reasons. For instance, a surgeon may want to minimize the size of the access incision and wish to slide smaller implant components into place rather than one large implant. Multiple component implants therefore allow for smaller implant components that can be implanted into a bone void through a smaller incision that a unitary implant used to fill an entire bone void by itself. Other considerations for employing multiple component implants may be limitations in the manufacturing molding process for creating the implant.

The present invention defines unique methods of assembly between components of a bone void filling implant. Such methods preferably take advantage of material flexibility of the implants being used and molding techniques to provide a flange or lap-type joint between components of a multiple component implant. Such a joint generally provides intraoperative alignment flexibility since an overlapping thinner outer flange extending outwardly from the side of the joint permits some degree of misalignment in all directions while still providing a gap free interface between adjacent components. A thicker inner portion or step extending inwardly from the side of the joint provides a rigid support for the flange to rest on and provides strength to the joint assembly. This uniform low profile joint is less noticeable under the skin surface. In reference to craniofacial applications, cosmetic implications are generally an issue. Having the ability to repair a bone void in a patient's cranium by assembling a multiple component implant without the need for fixation plates is an important consideration.

The present invention employs an overlapping flange feature on one component in contact with a recessed step feature on another component. This overlapping flange feature provides a means to accommodate some misalignment that can occur between the components and provides a smooth gap free outer surface contour to the implant. The flange feature can be fixed to step feature with screws or remain unfixed if the perimeter of the implant is adequately fixed to the surrounding bone.

In some embodiments, a plurality of joints can be employed for multiple component implants. The outer flange feature can be fixed to the step feature with screws only because of the overlapping nature of assembled adjacent components or remain unfixed if the perimeter of the implant is adequately fixed to the surrounding bone.

A first aspect of the present invention includes a craniofacial implant for filling a bone void in a cranium of a patient. According to one embodiment of this first aspect, the implant includes a first component having outer and inner surfaces, the outer and inner surfaces being curved in an inferior to posterior direction and a medial to lateral direction, the first component having a flange extending outwardly from a medial side surface thereof and a second component having outer and inner surfaces, the outer and inner surfaces being curved in an inferior to posterior direction and a medial to lateral direction, the second component having a recessed portion extending inwardly from a medial side surface thereof, wherein the first and second components are engageable to one another such that the medial side surfaces of the first and second components are adjacent one another and the flange of the first component is housed within the recessed portion of the second component.

According to another embodiment of this first aspect, the outer surfaces of the first and second components are convex and the inner surfaces of the first and second components are concave. The medial side surfaces of the first and second components are preferably planar in a direction perpendicular to at least a portion of the convex outer surface and at least a portion of the concave inner surface thereof. Preferably, the medial side surfaces of the first and second components form a first portion of a perimeter thereof, and the first and second components each further include curved lateral side surfaces that form a second portion of the perimeter thereof. The curved lateral side surfaces of the first and second components are preferably angled with respect to the medial side surfaces of the first and second components.

According to yet another embodiment of this first aspect, the flange of the first component preferably has medial and lateral ends, the medial end being adjacent to the medial side surface of the first component. The recessed portion of the first component preferably has medial and lateral ends, the medial end being adjacent to the medial side surface of the second component. Preferably, the proximal ends of the flange and the recessed portion are curved.

According to still yet another embodiment of this first aspect, an outer surface of the flange is angled toward the inner surface of the first component when the flange is in a neutral position. Preferably, the outer surface of the flange is contiguous with the outer surface of the first component when the flange is housed within the recessed portion. Preferably, the flange is deflectable.

A second aspect of the present invention is a method for filling a bone void in a cranium of a patient with a craniofacial implant. Preferably, the craniofacial implant has at least first and second components each having outer and inner surfaces, the outer and inner surfaces being curved in an inferior to posterior direction and a medial to lateral direction, the first component having a flange extending outwardly from a medial side surface thereof, and the second component having a recessed portion extending inwardly from a medial side surface thereof.

According to one embodiment of this second aspect, the method includes coupling a lateral side surface of the second component to a first portion of a perimeter of the bone void and contacting a lateral end of the flange of the first component with a lateral end of the recessed portion of the second component. The method further includes coupling a lateral side surface of the first component to a second portion of the perimeter of the bone void and moving at least a portion of the outer surface of the first component towards an inner surface of the second component such that an inner surface of the flange lies adjacent to an outer surface of the recessed portion from a medial end to the lateral end of the recessed portion.

According to another embodiment of this second aspect, when moving the at least a portion of the outer surface of the first component towards an inner surface of the second component, the medial end of the flange is rotated counterclockwise about a point defined by the lateral end of the flange in contact with the lateral end of the recessed portion. Preferably, when the inner surface of the flange lies adjacent to the outer surface of the recessed portion from the medial end to the proximal end of the recessed portion, the outer surfaces of the first and second components form a contiguous convex outer surface of the craniofacial implant.

According to yet another embodiment of this second aspect, the implant further includes a third component having outer and inner surfaces, the outer and inner surfaces being curved in an inferior to posterior direction and a medial to lateral direction, the third component having a flange extending outwardly from a medial side surface thereof. The method preferably further includes coupling a lateral side surface of the third component to a third portion of the perimeter of the bone void and contacting a lateral end of the flange of the third component with a lateral end of a recessed portion extending inwardly from a portion of the lateral side surface of the second component. The method preferably further includes moving at least a portion of the outer surface of the third component towards the inner surface of the second component such that an inner surface of the flange of the third component lies adjacent to an outer surface of the recessed portion of the second component from a medial end to the lateral end of the recessed portion of the second component.

A third aspect of the present invention is another method for filling a bone void in a cranium of a patient with a craniofacial implant. The implant preferably includes at least first and second components each having outer and inner surfaces, the outer and inner surfaces being curved in an inferior to posterior direction and a medial to lateral direction, the first component having a flange extending outwardly from a medial side surface thereof, and the second component having a recessed portion extending inwardly from a medial side surface thereof.

According to one embodiment of this third aspect, the method includes coupling a lateral side surface of the second component to a first portion of a perimeter of the bone void and contacting a lateral end of the flange of the first component with a medial end of the recessed portion of the second component. The method further includes sliding the lateral end of the flange of the first component from the medial end to the lateral end of the recessed portion of the second component and then coupling a lateral side surface of the first component to a second portion of the perimeter of the bone void. The method preferably further includes moving at least a portion of the outer surface of the first component towards an inner surface of the second component such that an inner surface of the flange lies adjacent to an outer surface of the recessed portion from a medial end to the lateral end of the recessed portion.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 4C is an exploded side view of the first and second implant components shown in FIG. 4A.

FIG. 4D is an assembled cross-sectional side view taken along line A-A of FIG. 4B of the first and second implant components.

FIGS. 6A-6C are cross-sectional side views of another embodiment of progressive steps of the assembly shown in FIG. 4D of the first and second implant components.

FIG. 7A is a perspective exploded view of one embodiment of first and second implant components prior to being assembled together in a flange-type joint of the present invention.

DETAILED DESCRIPTION

Figure 1A:
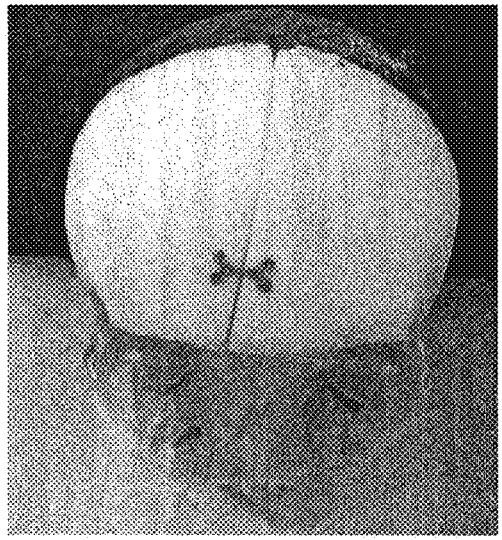
FIGS. 1A-B are top views of one embodiment of a prior art butt-type joint showing a fixation plate and screws affixing adjacent implant components.
Figure 1B:
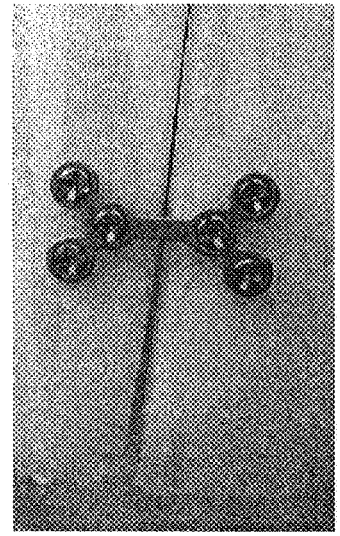
Figure 1C:
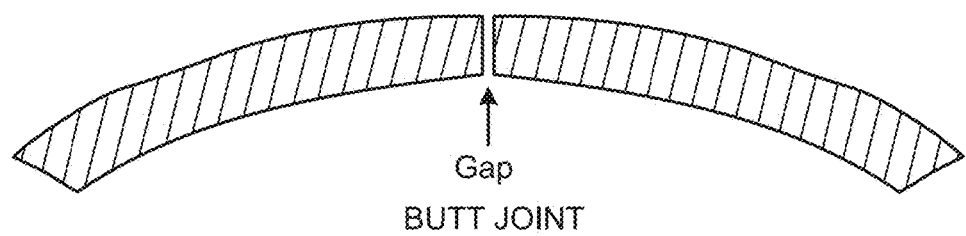
FIG. 1C is a side cross-sectional view of one embodiment of a butt-type joint shown in FIG. 1A.
Figure 2A:
FIG. 2A is a top view of one embodiment of a prior art biscuit-type joint showing a coupling member and first and second implant components and the coupling member coupling the first and second implant components.
Figure 2B:
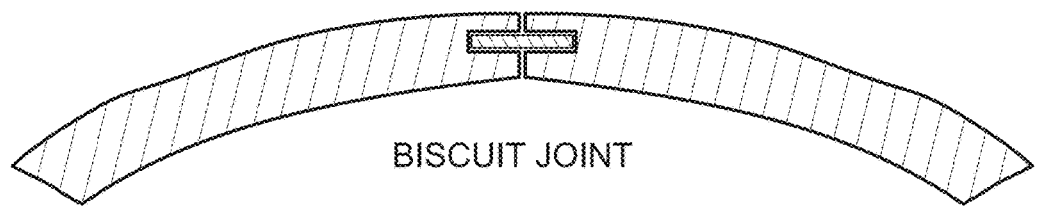
FIG. 2B is a side cross-sectional view of one embodiment of a biscuit-type joint shown in FIG. 2A.
Figure 3:
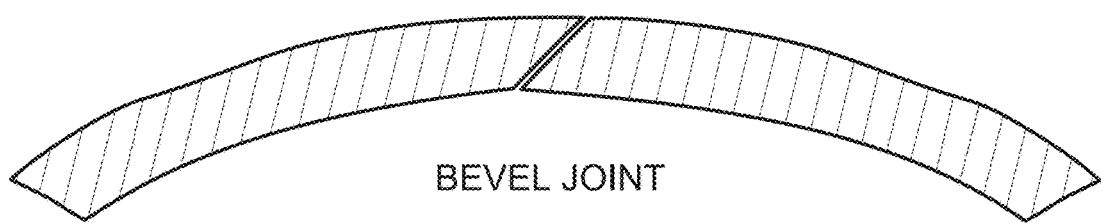
FIG. 3 is a side cross-sectional view of one embodiment of a prior art bevel-type joint having adjacent implant components.

Different prior art joint types for multiple component implants are shown in FIGS. 1A-3. FIGS. 1A-C show an example of a butt-type joint, FIGS. 2A-B show an example of a biscuit-type joint and FIG. 3 shows an example of a bevel-type joint. If any of these joint types are used to assemble adjacent components having a large joint line, each has a number of deficiencies. For instance, these designs generally result in at least some gap remaining between adjacent components after fixation along the joint line. Fixation members, such as plates and screws, for example, may be added to these designs to secure the engagement between adjacent components and provide rigidity to the assembled construct. Uneven loading may result in these joints such that motion and abrasion between adjacent components can occur. Further, uneven loading can cause deflection of components in these multiple component implants.

Figure 4A:
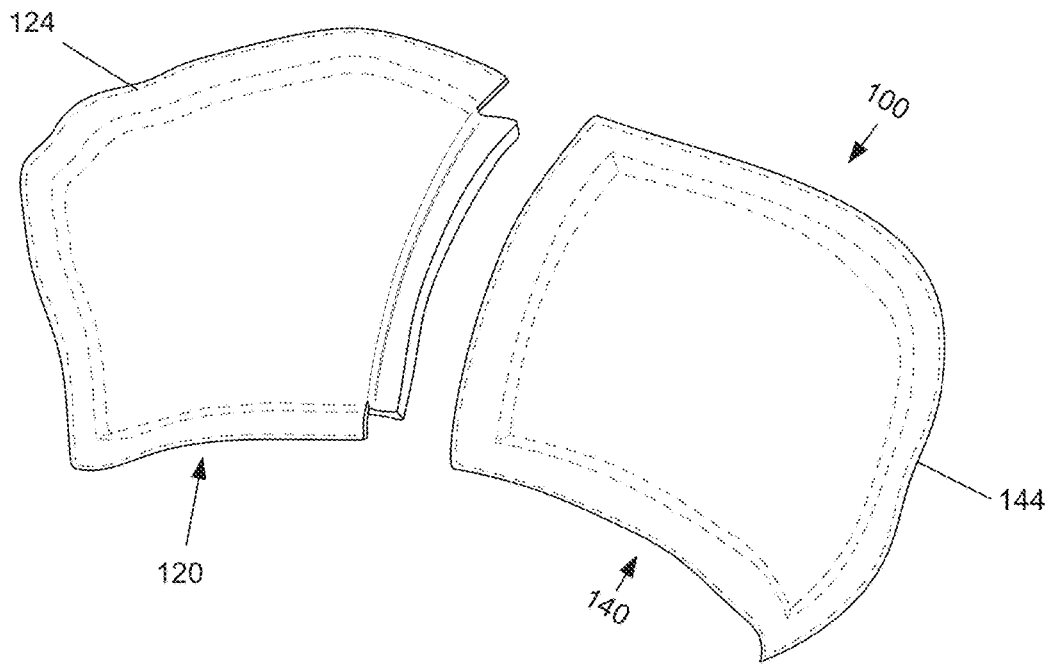
FIG. 4A shows one embodiment of a flange-type joint of the present invention showing an exploded view of a first implant component and a second implant component.
Figure 4B:
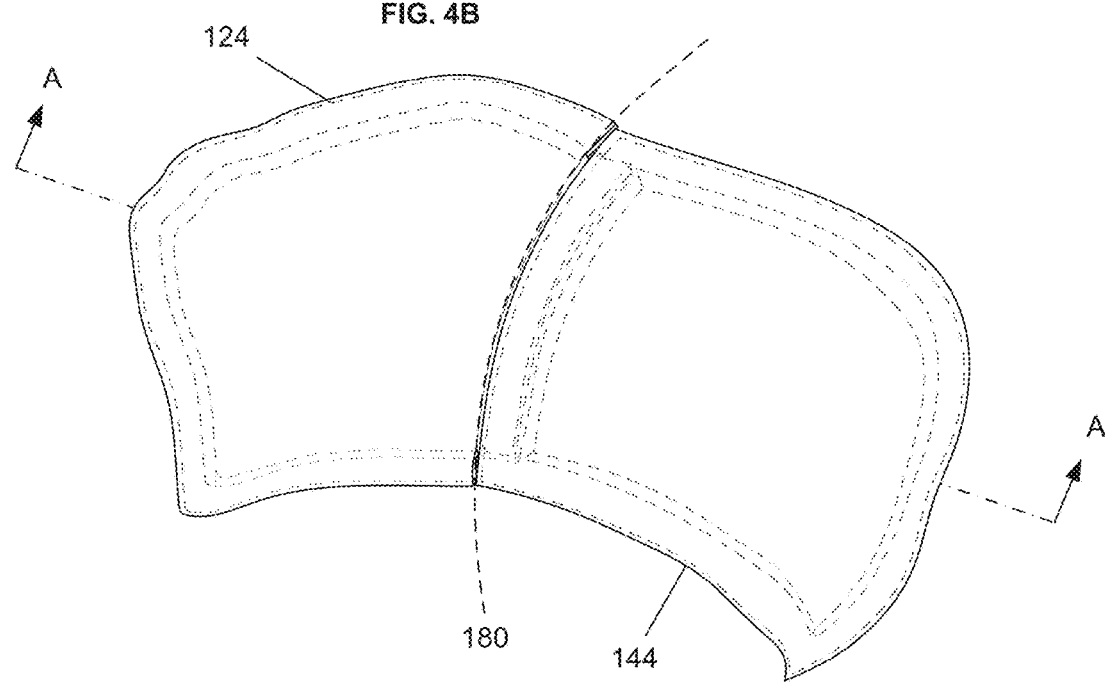
FIG. 4B shows an assembled view of the flange-type joint shown in FIG. 4A.

FIGS. 4A-D show one embodiment of a multiple component implant 100 of the present invention having a first implant component 120 and a second implant component 140. Implant 100 employs a flange or lap-type joint connecting first and second implant components 120, 140 along joint line 180 as shown in FIG. 4B. FIGS. 4A-B, show first implant component 120 and second implant component 140 in exploded and assembled perspective views. First and second implant components each have a medial side surface 122, 142 respectively as shown in FIGS. 4C-D. Medial side surfaces 122, 142 form a first portion of a perimeter of first and second implant components respectively. First and second implant components each further include a curved lateral side surface 124, 144 respectively. Curved lateral side surfaces 124, 144 form a second portion of a perimeter of first and second implant components 120, 140 respectively.

Implant 100 is preferably a craniofacial implant for filling a bone void in a cranium of a patient. As shown in FIG. 4C, first implant component 120 includes an outer surface 126 and an inner surface 128. Outer and inner surfaces 126, 128 are preferably curved in both an inferior to posterior direction and a medial to lateral direction. This curvature is generally the shape of portions of the frontal, temporal and parietal lobes of the cranium, for example.

First implant component 120 includes a flange 130 extending outwardly from medial side surface 122 thereof. Flange 130 includes a top surface 132, a bottom surface 134, and an edge surface 136 that is preferably rounded at a lateral end thereof. When flange 130 is in a neutral position as shown in FIG. 4C, edge surface 136 generally points downwardly. In other words, outer surface 132 of flange 130 is angled toward inner surface 128 of first component 120 when flange 130 is in the neutral position. Flange 130 extends from medial side surface 122 of first component 120 in a rigid fashion such that while flange 130 is generally deflectable, flange 130 tends to remain in the neutral position unless a substantial amount of force respective to the material of first component 120 and flange 130 is applied thereto. For example, flange 130 will deflect when sufficient forces are applied to either top surface 132 or bottom surface 134 thereof causing edge surface 136 to rotate in either a clockwise or counterclockwise direction, respectively.

Second implant component 140 includes an outer surface 146 and an inner surface 148. Outer and inner surfaces 146, 148 are preferably curved in both an inferior to posterior direction and a medial to lateral direction. Second implant component 140 includes a recess 150 extending inwardly from medial side surface 142 thereof. Recess 150 of second component 140 is configured to receive and house flange 130 of first component as shown in FIG. 4D. Medial side surfaces 122, 142 of the first and second components are preferably adjacent one another when flange 130 of first component 120 is housed within the recessed portion 150 of second component 140. Recess 150 extends from medial side surface 142 to a lateral end 156. Preferably, lateral end 156 is curved and adapted to receive rounded edge surface 136 of flange 130.

As shown in FIGS. 4C-4D, outer surfaces 126, 146 of the first and second components are convex and the inner surfaces 128, 148 of the first and second components are concave. Medial side surfaces 122, 142 of the first and second components are preferably planar in a direction perpendicular to at least a portion of the convex outer surface 126, 146 thereof and at least a portion of the concave inner surface 128, 148 thereof. Medial side surfaces 122, 142 of the first and second components 120, 140 form a first portion of a perimeter thereof, and the first and second components 120, 140 each further include curved lateral side surfaces 124, 144 that form a second portion of the perimeter thereof. The curved lateral side surfaces 124, 144 of the first and second components 120, 140 are preferably angled with respect to the medial side surfaces 122, 124 of the first and second components.

Figure 5A:
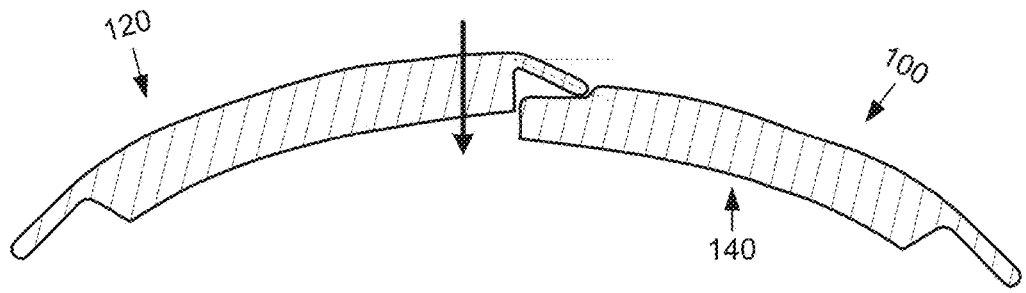
FIGS. 5A-5C are cross-sectional side views of one embodiment of progressive steps of the assembly shown in FIG. 4D of the first and second implant components.
Figure 5B:
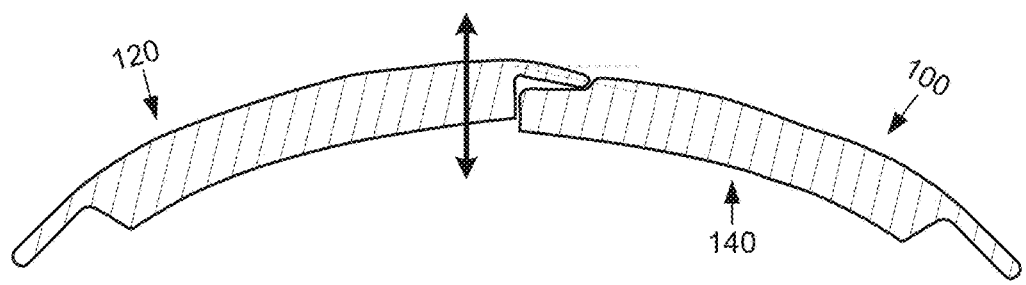
Figure 5C:
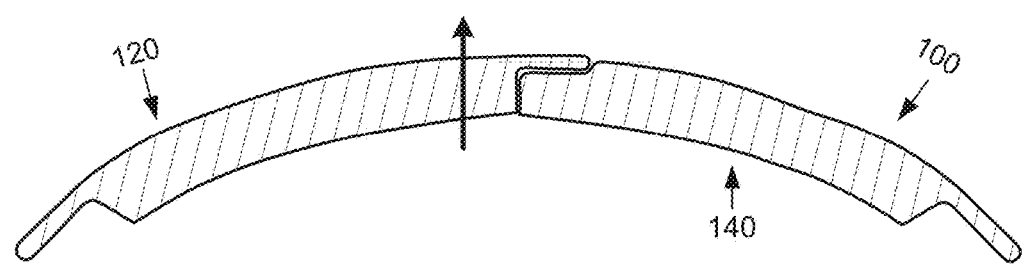

FIGS. 5A-5C are cross-sectional side views of one embodiment of progressive steps of the assembly shown in FIG. 4D of first and second implant components 120, 140. FIGS. 5A-5C, show the ability for the joint of implant 100 to adjust to a degree of misalignment between components 120, 140. This is an important feature of the present invention, since the CT or MRI scan upon which implant 100 is designed may have some dimensional variability. Also, it is possible that bone may grow between the time the scan is taken and the time of implantation surgery. Bone growth, for example, can introduce additional dimensional variability. Being able to fine tune the dimensions and alignment of implant 100 using the lap-type joint shown in FIGS. 5A-C, for example, is beneficial for improved surgical outcomes.

Figure 7B:
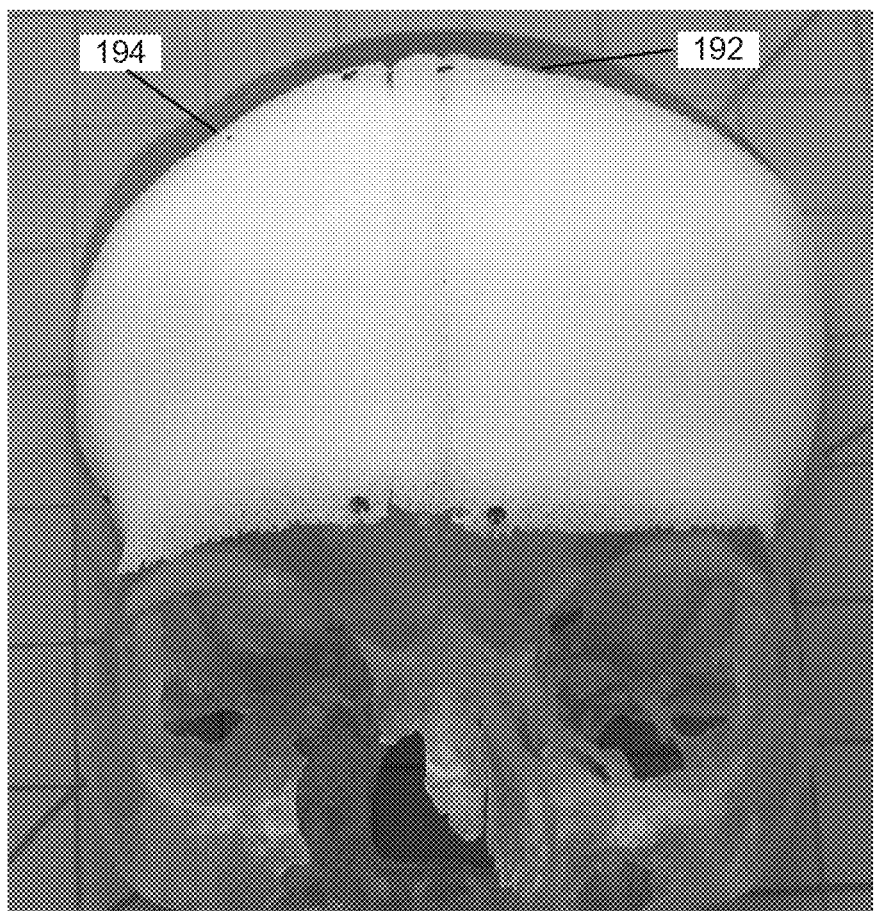
FIG. 7B is top assembled view of the first and second implant components shown in FIG. 7A and coupled to a bone void in a frontal lobe of a cranium.

One method of assembling first and second implant components of the present invention is shown in FIGS. 5A-C. First and second implant components are preferably used for filling a bone void in a cranium of a patient as shown in FIGS. 7A-B, for example. One method of filling the bone void includes coupling lateral side surface 144 of second component 140 to a first portion 192 of a perimeter of the bone void. As shown in FIG. 5A, the method includes contacting lateral end 136 of flange 130 of the first component 120 with lateral end 156 of recessed portion 150 of the second component 140. The method includes coupling lateral side surface 124 of first component 120 to a second portion 194 of the perimeter of the bone void, and moving at least a portion of the outer surface 126 of first component 120 towards inner surface 148 of second component 140 such that inner surface 134 of flange 130 lies adjacent an outer surface 155 of recessed portion 150 from medial end 142 to lateral end 156 of recessed portion 150. When moving the outer surface 126 of the first component 120 towards inner surface 148 of second component 140, medial end of flange 130 located medial side surface 124 is rotated counterclockwise about a point defined by lateral end 136 of flange 130 being in contact with lateral end 156 of recessed portion 150.

When inner surface 134 of flange 130 lies adjacent to outer surface 155 of recessed portion 150 from the medial end 142 to the lateral end 156 of recessed portion 150, the outer surfaces 126, 146 of the first and second components 120, 140 form a contiguous convex outer surface of the craniofacial implant as shown in FIG. 7B.

FIGS. 6A-6C are cross-sectional side views of another embodiment of progressive steps of the assembly shown in FIG. 4D of the first and second implant components. FIGS. 6A-6C show sliding flange 130 across step or recess 150 provides capacity to adjust the first and second components 120, 140 to ensure the width and length dimension of any separation between the medial side surfaces 122, 142 of first and second implant components 120, 140 is acceptable when components 120, 140 are assembled to one another. A gap between implant components greater than 2 mm may be visible under the skin after surgery. Flange 130 acts to cover the entire length and width of any potential gap between components 120, 140 since its thickness is preferably less than 2 mm, the flange joint transition between components 120, 140 provides a smooth outer contour and is preferably not noticeable under the skin after surgery.

Another method of filling the bone void is shown in FIGS. 7A-B, which includes coupling lateral side surface 144 of second component 140 to first portion 192 of perimeter of the bone void, then contacting lateral end 136 of flange 130 of first component 120 with medial end 142 of recessed portion 150 of second component 140. The method further includes sliding lateral end 136 of flange 130 of first component 120 from the medial end 142 to the lateral end 156 of the recessed portion 150 of the second component 140 and coupling lateral side surface 124 of the first component 120 to the second portion 194 of the perimeter of the bone void. The method further includes moving at least a portion of the outer surface 126 of first component 120 towards inner surface 148 of second component 140 such that inner surface 134 of flange 130 lies adjacent an outer surface 155 of recessed portion 150 from medial end 142 to lateral end 156 of recessed portion 150.

Figure 8:
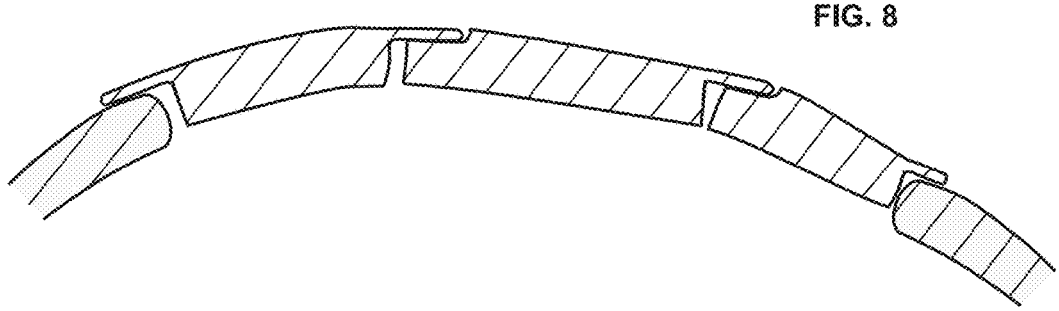
FIG. 8 is a cross-sectional side view of flange-type joints including a plurality of implant components assembled together.

FIG. 8 is a cross-sectional side view of flange-type joints including a plurality of implant components assembled together. Some components include both a recess and a flange, while other components include two flanges, for example. Regardless of how many components are used to fill a cranial void, for example, when the inner surface of a flange of one component lies adjacent to an outer surface of a recessed portion of another component from the medial end to the lateral end of the recessed portion of the another component, the outer surfaces of the components preferably form a contiguous convex outer surface of the craniofacial implant as shown in FIG. 8.

Figure 9:
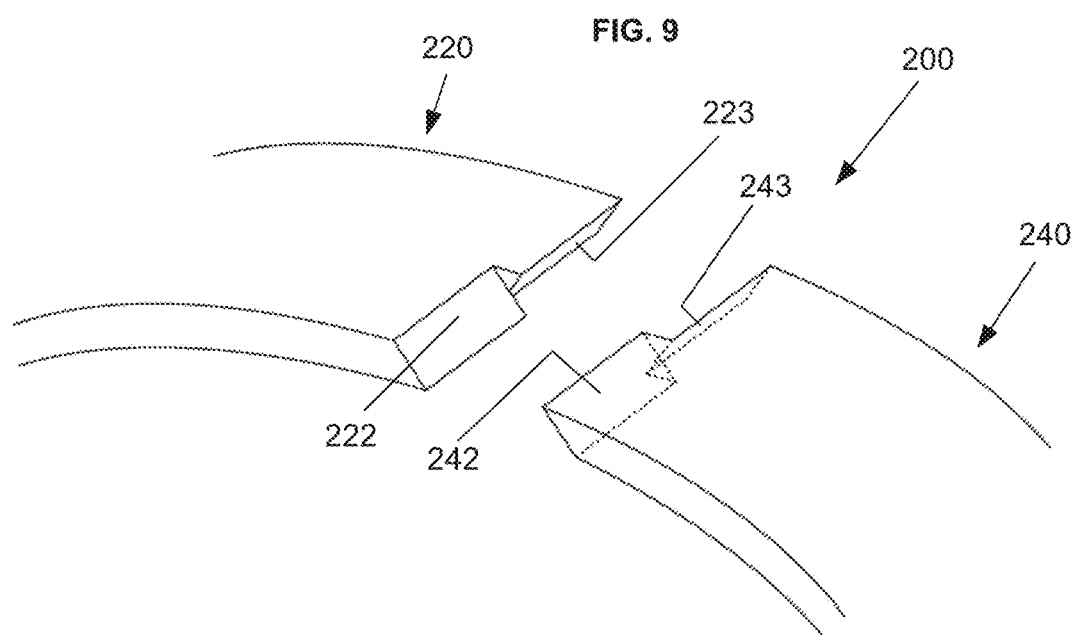
FIG. 9 is an exploded perspective view of one embodiment of the present invention of a complex bevel-type joint between first and second implant components having complimentary medial side surfaces.

FIG. 9 is an exploded perspective view of one embodiment of the present invention of a complex bevel-type joint between first and second implant components 220, 240 of implant 200 having complimentary medial side surfaces. When assembled, medial side surface 222 of first component 220 lies adjacent to medial side surface 242 of second component and medial side surface 223 of first component 220 lies adjacent to medial side surface 243 of second component 240. This configuration preferably provides some measure of support to an external load from both implant halves via the contacting medial side surfaces regardless of load location. The bevel on one side or the other preferably transfers the load to the other half of the implant. In a simple bevel joint, only a load placed on the overlapping bevel side that rests on the under bevel is supported by both halves of the implant. If the load were on only the under bevel side, it is free to flex away from the overlapping bevel if not fixed with screws and plates.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for filling a bone void in a cranium of a patient with a craniofacial implant having at least first and second components each having outer and inner surfaces, comprising:
    coupling a lateral side surface of the second component to a first portion of a perimeter of the bone void;
    contacting a lateral end of a deflectable flange of the first component with a lateral end of a recessed portion of the second component, the recessed portion being a cavity defined in the outer surface of the second component;
    coupling a lateral side surface of the first component to a second portion of the perimeter of the bone void; and
    rotating the deflectable flange about a point defined by a medial end of the flange when the lateral end of the flange is in contact with the lateral end of the recessed portion until an inner surface of the deflectable flange lies adjacent to an outer surface of the recessed portion from a medial end to the lateral end of the recessed portion and the outer surfaces of the first and second components form a contiguous convex outer surface of the craniofacial implant.

2. The method of claim 1, wherein the deflectable flange of the first component extends outwardly from a medial side surface thereof, and the recessed portion of the second component extends inwardly from a medial side surface thereof.

3. The method of claim 1, wherein the first and second components are separate and distinct components and both the first and second components are curved in both medial to lateral directions and inferior to posterior directions.

4. The method of claim 1, wherein rotating the deflectable flange moves at least a portion of the outer surface of the first component towards the inner surface of the second component.

5. The method of claim 1, wherein the deflectable flange is rotated counterclockwise about the point defined by the medial end of the deflectable flange.

6. The method of claim 1, wherein when the inner surface of the deflectable flange lies adjacent to the outer surface of the recessed portion, the inner surfaces of the first and second components form a contiguous concave inner surface of the craniofacial implant.

7. A method for filling a bone void in a cranium of a patient with a craniofacial implant having at least first and second component each having outer and inner surfaces, comprising:
  coupling a lateral side surface of the second component to a first portion of a perimeter of the bone void;
  contacting a deflectable flange of the first component with a recessed portion of the second component, the recessed portion being a cavity defined in the outer surface of the second component;
  rotating the deflectable flange about a point defined by a medial end of the deflectable flange when the deflectable flange is in contact with the second component until a lateral end of the deflectable flange lies on a plane defined by the outer surface of the first component;
  translating the lateral end of the deflectable flange until it contacts a lateral end of the recessed portion; and
  coupling a lateral side surface of the first component to a second portion of the perimeter of the bone void such that the outer surfaces of the first and second components form a contiguous convex outer surface of the craniofacial implant.

8. The method of claim 7, further comprising:
  rotating the deflectable flange until an inner surface of the deflectable flange lies adjacent to an outer surface of the recessed portion from a medial end to the lateral end of the recessed portion.

9. The method of claim 8, wherein rotating the deflectable flange moves at least a portion of the outer surface of the first component towards the inner surface of the second component.

10. The method of claim 8, wherein when the inner surface of the deflectable flange lies adjacent to the outer surface of the recessed portion.

11. The method of claim 8, wherein when the inner surface of the deflectable flange lies adjacent to the outer surface of the recessed portion, the inner surfaces of the first and second components form a contiguous concave inner surface of the craniofacial implant.

12. The method of claim 7, wherein the deflectable flange of the first component extends outwardly from a medial side surface thereof, and the recessed portion of the second component extends inwardly from a medial side surface thereof.

13. The method of claim 7, wherein the first and second components are curved in both medial to lateral directions and inferior to posterior directions.

14. The method of claim 7, wherein the deflectable flange is rotated counterclockwise about a point defined by the medial end of the deflectable flange.

15. A method for filling a bone void in a cranium of a patient with a craniofacial implant having at least first and second components each having outer and inner surfaces, comprising:
  coupling a lateral side surface of the second component to a first portion of a perimeter of the bone void;
  contacting an inner surface of a deflectable flange of the first component with an outer surface of a recessed portion, the recessed portion being a cavity defined in the outer surface of the second component;
  rotating the deflectable flange about a point defined by a medial end of the deflectable flange when the deflectable flange is in contact with the second component until a lateral end of the deflectable flange lies on a plane defined by the outer surface of the first component; and
  coupling a lateral side surface of the first component to a second portion of the perimeter of the bone void such that the outer surfaces of the first and second components form a contiguous convex outer surface of the craniofacial implant.

16. The method of claim 15, further comprising:
  contacting a lateral end of the deflectable flange of the first component with a lateral end of the recessed portion of the second component.

17. The method of claim 15, wherein the deflectable flange of the first component extends outwardly from a medial side surface thereof, and the recessed portion of the second component extends inwardly from a medial side surface thereof.

18. The method of claim 15, wherein the first and second components are curved in both medial to lateral directions and inferior to posterior directions.

* * * * *